US011026659B2

(12) United States Patent
Nishihara et al.

(10) Patent No.: US 11,026,659 B2
(45) Date of Patent: Jun. 8, 2021

(54) ULTRASOUND DIAGNOSIS APPARATUS

(71) Applicant: Toshiba Medical Systems Corporation, Otawara (JP)

(72) Inventors: Kuramitsu Nishihara, Otawara (JP); Akihiro Kakee, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1196 days.

(21) Appl. No.: 14/563,238

(22) Filed: Dec. 8, 2014

(65) Prior Publication Data
US 2015/0094586 A1  Apr. 2, 2015

Related U.S. Application Data

(63) Continuation of application No. PCT/JP2013/067002, filed on Jun. 20, 2013.

(30) Foreign Application Priority Data

Jun. 22, 2012 (JP) .............................. JP2012-141239
Jun. 20, 2013 (JP) .............................. JP2013-129731

(51) Int. Cl.
A61B 8/08 (2006.01)
A61B 8/00 (2006.01)
(Continued)

(52) U.S. Cl.
CPC .............. *A61B 8/5207* (2013.01); *A61B 8/00* (2013.01); *A61B 8/14* (2013.01); *G01S 7/52023* (2013.01);
(Continued)

(58) Field of Classification Search
CPC ........... A61B 8/5207; A61B 8/00; A61B 8/08; A61B 8/14; G01S 7/52023; G01S 7/52034; G01S 15/895
(Continued)

(56) References Cited

U.S. PATENT DOCUMENTS 5,482,044 A * 1/1996 Lin ...................... G01S 7/52025
                                                        600/443
5,628,322 A * 5/1997 Mine .................... G01N 29/036
                                                        600/453
(Continued)

FOREIGN PATENT DOCUMENTS

JP  H04-164441 A1  6/1992
JP  H07-000394 A1  1/1995
(Continued)

OTHER PUBLICATIONS

Machine translation of H04-164441 from J-Plat Pat; detailed description and claims.*

(Continued)

*Primary Examiner* — Michael J Tsai
*Assistant Examiner* — Johnathan Maynard
(74) *Attorney, Agent, or Firm* — Oblon, McClelland, Maier & Neustadt, L.L.P.

(57) ABSTRACT

An ultrasound diagnosis apparatus according to an embodiment includes a receiving unit and a changing unit. The receiving unit outputs an ultrasound received signal. The changing unit obtains, in accordance with a change in a spatial frequency of ultrasound image data subject to an imaging processing, a group of parameters related to a frequency characteristic of an imaging received signal that is output by the receiving unit as the ultrasound received signal to be used in the imaging processing and changes a center frequency and a frequency band to be used in the imaging processing performed on the imaging received signal, on a basis of the obtained group of parameters.

4 Claims, 11 Drawing Sheets

(51) Int. Cl.
  *G01S 15/89*  (2006.01)
  *G01S 7/52*  (2006.01)
  *A61B 8/14*  (2006.01)

(52) U.S. Cl.
  CPC ........ *G01S 7/52034* (2013.01); *G01S 15/895* (2013.01)

(58) Field of Classification Search
  USPC .......................................................... 600/443
  See application file for complete search history.

(56) References Cited

U.S. PATENT DOCUMENTS

| | | | | |
|---|---|---|---|---|
| 6,251,075 | B1* | 6/2001 | Hashimoto | A61B 8/00 600/453 |
| 6,419,632 | B1* | 7/2002 | Shiki | A61B 8/06 600/443 |
| 2012/0095323 | A1* | 4/2012 | Eskandari | A61B 8/5269 600/411 |

FOREIGN PATENT DOCUMENTS

| | | | | |
|---|---|---|---|---|
| JP | H07-236640 | A1 | 9/1995 | |
| JP | 2006230919 | * | 7/2006 | ............... A61B 8/00 |
| JP | 2006230919 | A * | 9/2006 | |
| JP | 2008-161262 | A1 | 7/2008 | |

OTHER PUBLICATIONS

Eskandari, H., Goksel, O., Salcudean, S. E., & Rohling, R. (2011). Bandpass sampling of high-frequency tissue motion. IEEE transactions on ultrasonics, ferroelectrics, and frequency control, 58(7), 1332-1343. (Year: 2011).*

Eskandari, H., Goksel, O., Salcudean, S. E., & Rohling, R. (2011). Bandpass sampling of high-frequency tissue motion. IEEE transactions on ultrasonics, ferroelectrics, and frequency control, 58(7), 1332-1343. (Year: 2011).*

International Search Report dated Jul. 16, 2013 for PCT/JP2013/067002 filed on Jun. 20, 2013 with English Translation.

International Written Opinion dated Jul. 16, 2013 for PCT/JP2013/067002 filed on Jun. 20, 2013.

* cited by examiner

| PEAK FREQUENCY HAVING n-th HIGHEST INTENSITY |
| CENTER OF MASS FREQUENCY |
| BANDWIDTH |
| FRACTIONAL BANDWIDTH |
| UPPER LIMIT FREQUENCY |
| LOWER LIMIT FREQUENCY |
| TRANSMISSION FREQUENCY |
| FREQUENCY EQUAL TO INTEGER MULTIPLE OF TRANSMISSION FREQUENCY |

ULTRASOUND DIAGNOSIS APPARATUS

CROSS-REFERENCE TO RELATED APPLICATIONS

This application is a continuation of PCT international application Ser. No. PCT/JP2013/067002 filed on Jun. 20, 2013 which designates the United States, incorporated herein by reference, and which claims the benefit of priority from Japanese Patent Application No. 2012-141239, filed on Jun. 22, 2012, and Japanese Patent Application No. 2013-129731, filed on Jun. 20, 2013, the entire contents of which are incorporated herein by reference.

FIELD

Embodiments described herein relate generally to an ultrasound diagnosis apparatus.

BACKGROUND

Conventionally, ultrasound diagnosis apparatuses reduce data amounts by performing a thinning-out processing (called a "decimation") on received signals for the purpose of reducing the number of times a calculation needs to be performed before ultrasound image data is generated. Furthermore, ultrasound diagnosis apparatuses change sampling frequencies of output data that is output for the purpose of generating images, by changing thinning-out rates (decimation rates) in accordance with spatial frequency to imaging processing. Ultrasound diagnosis apparatus thus accommodate both the reduction of data amounts and spatial resolutions.

According to the conventional technique, however, the sensitivity and the spatial resolution of ultrasound image data are not necessarily optimal, in some situations, depending on the decimation rate.

DETAILED DESCRIPTION

An ultrasound diagnosis apparatus according to an embodiment includes a receiving unit and a changing unit. The receiving unit outputs an ultrasound received signal. The changing unit obtains, in accordance with a change in a spatial frequency of ultrasound image data subject to an imaging processing, a group of parameters related to a frequency characteristic of an imaging received signal that is output by the receiving unit as the ultrasound received signal to be used in the imaging processing and changes a center frequency and a frequency band to be used in the imaging processing performed on the imaging received signal, on a basis of the obtained group of parameters.

Exemplary embodiments of an ultrasound diagnosis apparatus will be explained in detail below, with reference to the accompanying drawings.

Figure 1:
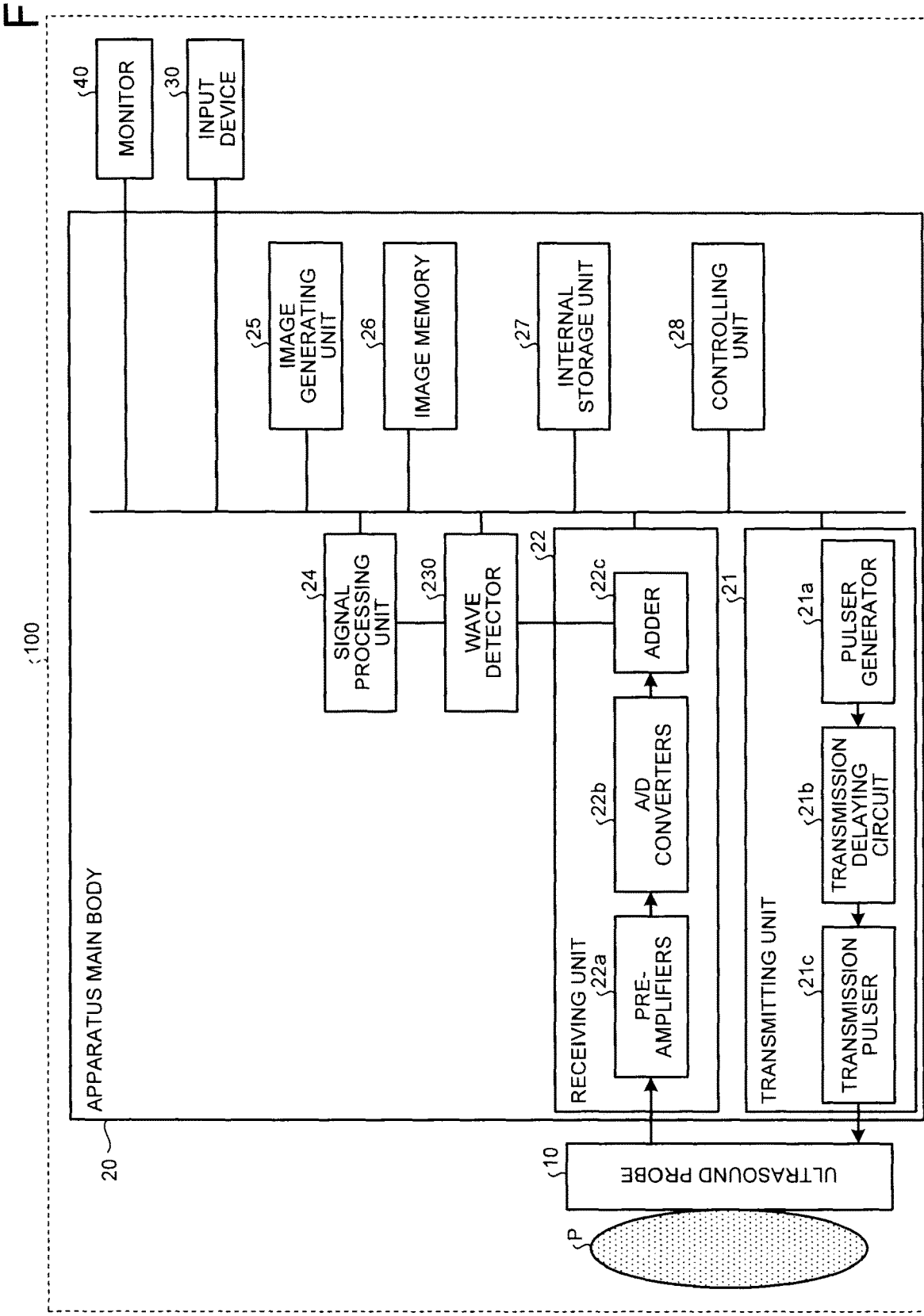
FIG. 1 is a diagram of an exemplary configuration of a conventional ultrasound diagnosis apparatus.

First, before explaining the exemplary embodiments of the ultrasound diagnosis apparatus discussed herein, a conventional ultrasound diagnosis apparatus will be explained with reference to FIG. 1. FIG. 1 is a diagram of an exemplary configuration of the conventional ultrasound diagnosis apparatus. As shown in FIG. 1, a conventional ultrasound diagnosis apparatus 100 includes an ultrasound probe 10, an apparatus main body 20, an input device 30, and a monitor 40.

The ultrasound probe 10 includes, as a plurality of acoustic elements (a group of acoustic elements), a plurality of piezoelectric transducer elements, for example, which generate an ultrasound wave based on a drive signal supplied from a transmitting unit 21 included in the apparatus main body 20 (explained later). Furthermore, the ultrasound probe 10 receives a reflected wave from an examined subject (hereinafter, a "subject") P and converts the received reflected wave into an electric signal. Furthermore, the ultrasound probe 10 includes matching layers included in the piezoelectric transducer elements, as well as a backing member that prevents ultrasound waves from propagating rearward from the piezoelectric transducer elements.

When an ultrasound wave is transmitted from the ultrasound probe 10 to the subject P, the transmitted ultrasound wave is repeatedly reflected on a surface of discontinuity of acoustic impedances at a tissue in the body of the subject P and is received as a reflected-wave signal by the plurality of piezoelectric transducer elements included in the ultrasound probe 10. The amplitude of the received reflected-wave signal is dependent on the difference of the acoustic impedances on the surface of discontinuity on which the ultrasound wave is reflected. When the transmitted ultrasound pulse is reflected on the surface of a flowing bloodstream or a cardiac wall and the like, the reflected-wave signal is, due to the Doppler effect, subject to a frequency shift, depending on a velocity component of the moving members with respect to the ultrasound wave transmission direction.

The input device 30 includes a mouse, a keyboard, a button, a panel switch, a touch command screen, a foot switch, a trackball, and the like. The input device 30 receives various types of setting requests from an operator of the ultrasound diagnosis apparatus 100 and transfers the received various types of setting requests to the apparatus main body 20.

The monitor 40 displays a Graphical User Interface (GUI) used by the operator of the ultrasound diagnosis apparatus 100 to input the various types of setting requests through the input device 30 and displays ultrasound images and the like generated by the apparatus main body 20.

The apparatus main body 20 is an apparatus that exercises overall control of ultrasound image taking processing, and more specifically, is an apparatus that generates ultrasound image data based on the reflected wave received by the ultrasound probe 10. As shown in FIG. 1, for example, the apparatus main body 20 includes the transmitting unit 21, a receiving unit 22, a wave detector 230, a signal processing unit 24, an image generating unit 25, an image memory 26, an internal storage unit 27, and a controlling unit 28.

As shown in FIG. 1, the transmitting unit 21 includes a pulser generator 21a, a transmission delaying circuit 21b, and a transmission pulser 21c and supplies the drive signal to the ultrasound probe 10. The pulser generator 21a repeatedly generates a pulse for forming a transmission ultrasound wave at a predetermined frequency. While having mutually-different transmission delay periods as a result of going through the transmission delaying circuit 21b, the pulses apply a voltage to the transmission pulser 21c. In other words, the transmission delaying circuit 21b applies a transmission delay period that is required to focus the ultrasound wave generated by the ultrasound probe 10 into the form of a beam and to determine transmission directivity and that corresponds to each of the piezoelectric transducer elements, to each of the pulses generated by the pulser generator 21a. Furthermore, the transmission pulser 21c applies a drive signal (a drive pulse) to the ultrasound probe 10 with timing based on the pulses.

After the drive pulse is transferred from the transmission pulser 21c to the piezoelectric transducer elements provided inside the ultrasound probe 10 via a cable, the drive pulse is converted from an electric signal into a mechanical vibration at each of the piezoelectric transducer elements. The mechanical vibrations are transmitted as ultrasound waves on the inside of the subject's body. In this situation, the ultrasound waves having mutually-different transmission delay periods in correspondence with the piezoelectric transducer elements are focused and propagate in predetermined directions. In other words, the transmission delaying circuit 21b arbitrarily adjusts the transmission directions from the piezoelectric transducer element surfaces, by varying the transmission delay periods applied to each of the pulses.

In this situation, the transmitting unit 21 has a function to be able to instantly change the transmission frequency, the transmission drive voltage, and the like, for the purpose of executing a predetermined scan sequence based on an instruction from the controlling unit 28 (explained later). In particular, the configuration to change the transmission drive voltage is realized by using a linear-amplifier-type transmitting circuit of which the value can be instantly switched or by using a mechanism that electrically switches between a plurality of power source units.

After reflected waves of the ultrasound waves transmitted by the ultrasound probe 10 have reached the piezoelectric transducer elements provided inside the ultrasound probe 10, the reflected waves are converted from the mechanical vibrations to analog electric signals (reflected-wave signals) at the piezoelectric transducer elements, so that the analog electric signals are input to the receiving unit 22. As shown in FIG. 1, the receiving unit 22 includes pre-amplifiers 22a, Analog/Digital (A/D) converters 22b, and an adder 22c, and outputs data obtained by performing various types of processing on the reflected-wave signals received by the ultrasound probe 10, to the wave detector 230 provided at the subsequent stage.

The pre-amplifiers 22a amplifies the reflected-wave signals in correspondence with channels (or in correspondence with the transducer elements) and to adjust the gains thereof. The A/D converters 22b convert the gain-corrected reflected-wave signals into digital data, by applying A/D conversions to the gain-corrected reflected-wave signals. The pre-amplifiers 22a and the A/D converters 22b are provided in correspondence with the channels (or in correspondence with the transducer elements). In other words, the pre-amplifiers 22a and the A/D converters 22b are both made up of a plurality of circuits. The adder 22c applies a reception delay period required to determine reception directivity to the digital data. Furthermore, the adder 22c performs an addition processing on pieces of digital data to which the reception delay periods have been applied. As a result of the addition processing performed by the adder 22c, reflected components from the direction corresponding to the reception directivity of the reflected-wave signals are emphasized. In other words, the adder 22c performs a so-called beam forming processing.

As explained above, the transmitting unit 21 and the receiving unit 22 controls the transmission directivity and the reception directivity in the ultrasound wave transmissions and receptions. In other words, the transmitting unit 21 functions as a transmission beam former, whereas the receiving unit 22 functions as a reception beam former.

The wave detector 230 performs a data interpolation processing and a decimation processing, by performing a frequency modulating processing, a filtering processing, and the like on the data output from the adder 22c. The data output from the wave detector 230 is output as reflected-wave data to the signal processing unit 24 provided at the subsequent stage. Processing performed by the wave detector 230 will be explained in detail later.

The signal processing unit 24 receives the reflected-wave data from the wave detector 230 and to generate data (B-mode data) in which the intensity of each signal is expressed by a degree of brightness, by performing a logarithmic amplification, an envelope detection processing, and the like on the received reflected-wave data. Furthermore, the signal processing unit 24 performs a frequency analysis so as to obtain velocity information from the reflected-wave data received from the wave detector 230, extracts bloodstream, tissues, and contrast-agent echo components that are under the influence of the Doppler effect, and further generates data (Doppler data) obtained by extracting moving member information such as an average velocity, a dispersion, a power, and the like for a plurality of points.

The image generating unit 25 generates ultrasound image data from the data generated by the signal processing unit 24. In other words, from the B-mode data, the image generating unit 25 generates B-mode image data in which the intensity of the reflected wave is expressed by a degree of brightness. Furthermore, from the Doppler data, the image generating unit 25 generates average velocity image data, dispersion image data, and power image data each expressing the moving member information, or generates color Doppler image data, which is an image combining any of these types of image data. Furthermore, the image generating unit 25 is also able to generate synthesized image data in which text information of various parameters, scale graduations, body marks, and the like are synthesized with the ultrasound image data.

In this situation, the image generating unit 25 converts (by performing a scan convert processing) a scanning line signal sequence from an ultrasound scan into a scanning line signal sequence in a video format used by, for example, television and generates ultrasound image data serving as a display-purpose image. Furthermore, as various types of image processing other than the scan convert processing, the image generating unit 25 performs, for example, an image processing (a smoothing processing) to re-generate a brightness-average image or an image processing (an edge enhancement processing) using a differential filter within images, while using a plurality of image frames obtained after the scan convert processing is performed.

Furthermore, the image generating unit 25 has installed therein a storage memory that stores therein image data and is able to perform three-dimensional image re-constructing processing and the like. Furthermore, after a diagnosis processing, for example, the operator is able to invoke one or more images that were recorded during a medical examination, from the storage memory installed in the image generating unit 25.

The B-mode data and the Doppler data are the ultrasound image data before the scan convert processing is performed. The data generated by the image generating unit 25 is the display-purpose ultrasound image data obtained after the scan convert processing is performed. The B-mode data and the Doppler data may also be referred to as raw data.

The image memory 26 is a memory for storing therein the display-purpose image data generated by the image generating unit 25. Furthermore, the image memory 26 is also able to store therein the data generated by the signal processing unit 24. After a diagnosis processing, for example, the operator is able to invoke the B-mode data or the Doppler data stored in the image memory 26. The invoked data in this situation serves as the display-purpose ultrasound image data via the image generating unit 25. Furthermore, the image memory 26 is also able to store therein the reflected-wave data output by the wave detector 230.

The internal storage unit 27 stores therein various types of data such as a control computer program (hereinafter, a "control program") to realize the ultrasound wave transmissions and receptions, image processing, and display processing, as well as diagnosis information (e.g., patients' IDs, medical doctors' observations), diagnosis protocols, and various types of body marks. Furthermore, the internal storage unit 27 may be used, as necessary, for storing therein any of the image data stored in the image memory 26. Furthermore, it is possible to transfer the data stored in the internal storage unit 27 to external apparatuses via an interface (not shown). Furthermore, the internal storage unit 27 is also able to store therein data that has been transferred thereto from external apparatuses via an interface (not shown).

The controlling unit 28 controls the entire processing performed by the ultrasound diagnosis apparatus 100. More specifically, based on the various types of setting requests input by the operator via the input device 30 and various types of control programs and various types of data read from the internal storage unit 27, the controlling unit 28 controls processing performed by the transmitting unit 21, the receiving unit 22, the wave detector 230, the signal processing unit 24, and the image generating unit 25. Furthermore, the controlling unit 28 exercises control so that the monitor 40 displays the display-purpose ultrasound image data stored in the image memory 26 and the internal storage unit 27.

Figure 2:
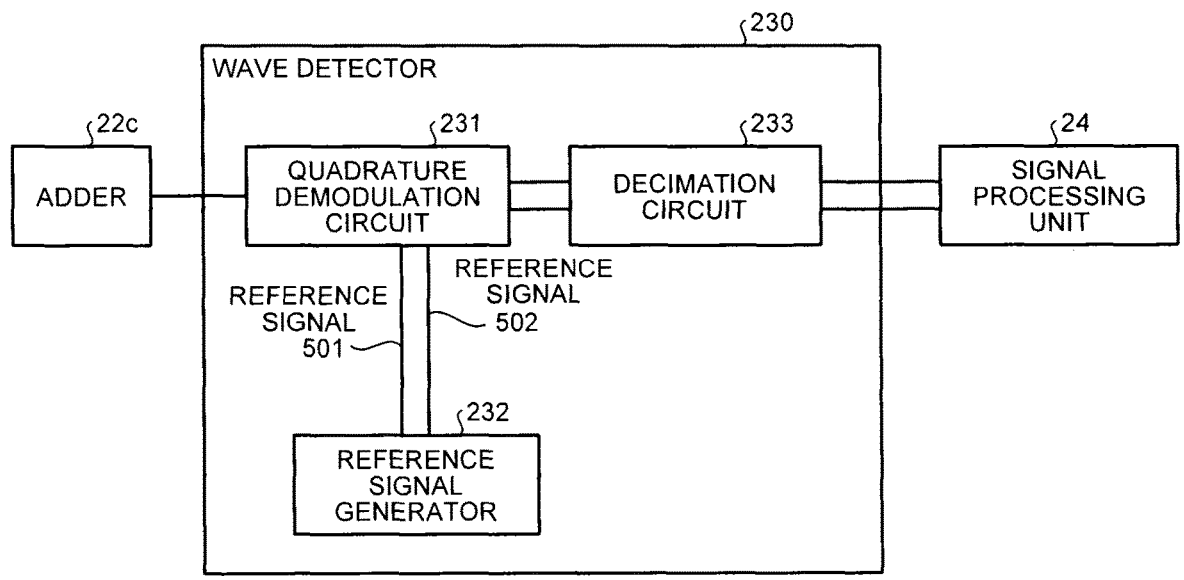
FIG. 2 is a diagram of an exemplary configuration of the conventional wave detector shown in FIG. 1.

The exemplary configuration of the conventional ultrasound diagnosis apparatus 100 has thus been explained. Being configured as described above, the conventional ultrasound diagnosis apparatus 100 performs the data interpolation processing and the decimation processing by performing the frequency modulating processing, the filtering processing, and the like while employing the wave detector 230. As a result of the decimation processing performed by the wave detector 230, the ultrasound diagnosis apparatus 100 reduces the amounts of data output to the signal processing unit 24 and the image generating unit 25 and reduces the number of times the calculation needs to be performed before the ultrasound image data is generated. Next, the wave detector 230 will be explained in detail below with reference to FIG. 2 and the like. FIG. 2 is a diagram of an exemplary configuration of the conventional wave detector shown in FIG. 1.

Figure 3:
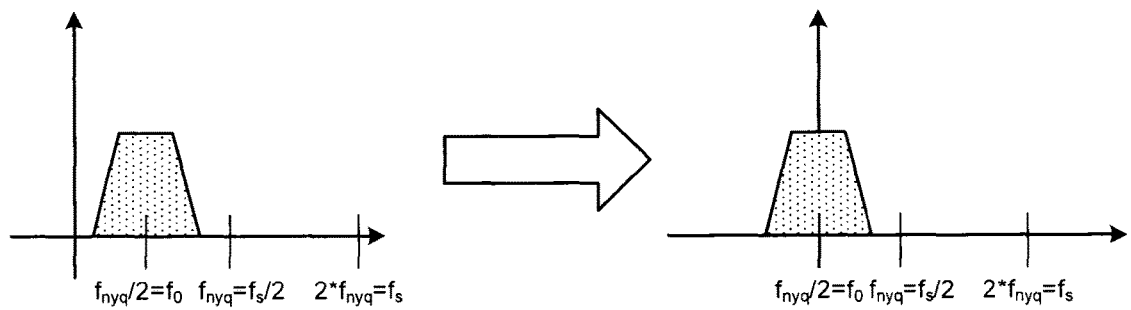
FIG. 3 is a drawing for explaining an outline of a frequency modulating processing realized by a quadrature demodulation processing.

As illustrated in FIG. 2, the wave detector 230 includes a quadrature demodulation circuit 231, a reference signal generator 232, and a decimation circuit 233. The quadrature demodulation circuit 231 converts the output signal from the adder 22c into an in-phase signal (an "I signal") and a quadrature-phase signal (a "Q signal") in a baseband bandwidth. FIG. 3 is a drawing for explaining an outline of the frequency modulating processing realized by a quadrature demodulation processing. In FIG. 3, the horizontal axis represents the frequencies, whereas the vertical axis represents the intensity of the ultrasound received signal corresponding to the each of the frequencies. As shown in FIG. 3, as a result of the quadrature demodulation processing using reference signals of which the frequency is $f_0$, $(=f_{nyq}/2)$, the frequency band of the ultrasound received signal is subject to a frequency shift to 0 hertz (Hz). As a result, as shown in FIG. 3, while the data to be dealt with corresponds to the same time length, it is possible to be lower sampling frequency $f_{nyq}$ by performing the quadrature demodulation processing and decimation processing. Furthermore, sampling frequency can be lower than $f_{nyq}$ by using low pass filter which has lower cut-off frequency than $f_{nyq}$.

More specifically, as shown in FIG. 2, the data output from the adder 22c is multiplied by a reference signal 501 and a reference signal 502 of which the frequencies are $f_0$, respectively, by the quadrature demodulation circuit 231. The reference signal 501 and the reference signal 502 are generated by the reference signal generator 232. Generally speaking, the frequency $f_0$ is conventionally set to be the center frequency of an ultrasound received signal. The frequency $f_0$ is one of the parameters that are set in advance together with a transmission condition and the like. In this situation, the reference signal 501 and the reference signal 502 are signals of which the phases are different from each other by 90 degrees. In other words, the reference signal 501 can be expressed as a signal "$\sin(2\pi f_0 t)$", whereas the reference signal 502 can be expressed as a signal "$\cos(2\pi f_0 t)$".

The quadrature demodulation circuit 231 performs the quadrature demodulation processing that uses the reference signal 501 and the reference signal 502 on the ultrasound received signal output from the adder 22c. As a result, the frequency $f_0$ of the ultrasound received signal is frequency-modulated to the baseband (0 Hz). After that, the signals (the I signal and the Q signal) output from the quadrature demodulation circuit 231 are subject to a decimation processing performed by the decimation circuit 233. The data on which the decimation processing has been performed by the decimation circuit 233 is then output to the signal processing unit 24 as the reflected-wave data.

In this situation, the decimation processing (the decimation processing) by the decimation circuit 233 is performed for the purpose of reducing the amount of data that is dealt with at the subsequent stages. The higher the decimation rate (the decimation rate) is, the larger the reduction of data volume becomes. However, in that situation, the sampling frequency for the data becomes lower, and the temporal resolution also becomes lower. When the temporal resolution becomes lower due to the lowering of the sampling frequency, the spatial resolution of the ultrasound image data output to the monitor 40 becomes lower. For this reason, it is necessary to properly set a decimation rate in accordance with the spatial frequency subject to the actual imaging processing. More specifically, the decimation processing performed by the decimation circuit 233 is possible if the spatial frequency (the pixel rate) subject to the imaging processing is lower than the sampling frequency used in the analog/digital conversion performed by the A/D converters 22*b*. Generally speaking, the sampling frequency used by the A/D converters 22*b* is fixed in many situations.

As explained above, the higher the decimation rate is, the higher is the effect of the data reduction. However, in that situation, the sampling frequency for the data becomes lower, and the temporal resolution (the spatial resolution) also becomes lower. Furthermore, if a decimation processing is simply performed, noise occurs due to aliasing. For this reason, it is necessary to perform a Low Pass Filter (LPF) processing that takes the Nyquist frequency (the aliasing frequency) into consideration, on the data resulting from the quadrature demodulation processing. Although the exemplary configuration illustrated in FIG. 2 does not show any processing unit (hereinafter, an "LPF") that performs the LPF processing, the LPF may be provided between the quadrature demodulation circuit 231 and the decimation circuit 233. Alternatively, the LPF may be provided in the decimation circuit 233. It will be assumed hereinafter that the decimation circuit 233 has the LPF provided therein. In many situations, such an LPF also has an effect of inhibiting a harmonic component "$2*f_0$", which secondarily occurs due to the quadrature demodulation processing.

The processing performed by the wave detector 230 included in the conventional ultrasound diagnosis apparatus 100 shown in FIG. 1 has thus been explained.

In this situation, the image size of the ultrasound image data generated by the image generating unit 25 is, in many situations, constant to a certain extent, in accordance with the size of a monitor or the resolution of a monitor. Furthermore, although it is possible to change the image output region in some situations, even in those situations, it is often the case that a selection needs to be made from a limited number of options. When the image taking region subject to an imaging processing is changed by changing the depth to be displayed with ultrasound image data or by panning/zooming the image, if the image size is constant, the spatial frequency subject to the imaging processing is to be changed. In that situation, the conventional system changes the sampling frequency for the data to be output to the signal processing unit 24 (hereinafter, "output data"), in accordance with the spatial frequency subject to the imaging processing, by changing the decimation rate of the decimation circuit 233. As a result, according to the conventional technique, the effect of reducing the amount of data is maintained while the spatial resolution is adjusted. For example, let us discuss a situation in which the image size in the depth direction of ultrasound image data is fixed to 1000 pixels. In this situation, if data that expresses up to the depth of "10 cm" with 10000 pieces of data is input to the decimation circuit 233, the decimation rate is calculated as "1000/10000=1/10". In contrast, if the depth is changed from "10 cm" to "20 cm", data that expresses up to the depth of "20 cm" with 20000 pieces of data is input to the decimation circuit 233. Thus, the decimation rate was changed to "1/20". In that situation, the entirety of the ultrasound image data has a low spatial resolution, and the spatial resolution in that situation is dependent on the display mode such as the resolution of the display monitor.

Furthermore, in the conventional system illustrated in FIGS. 1 and 2, the frequency $f_0$ of the reference signals in the quadrature demodulation processing is changed, in many situations, in accordance with the propagation time period (the depth), in consideration of the impact of a frequency-dependent attenuation caused in the propagation of the ultrasound wave. Furthermore, in the conventional system illustrated in FIGS. 1 and 2, the passband used in the actual imaging processing is not necessarily always set to the widest possible passband that is allowed within the range of the frequency band restricted by the Nyquist frequency. In the conventional configuration illustrated in FIGS. 1 and 2, the passband used in the actual imaging processing is, in many situations, set to a range that is even narrower than the range restricted by the Nyquist frequency, in accordance with the characteristics of the ultrasound received signal or the received signal used in the imaging processing. In other words, in the conventional system illustrated in FIGS. 1 and 2, the passband used in the imaging processing is the narrower of the passband set according to the decimation rate and the passband restricted by the Nyquist frequency.

The conventional configurations illustrated in FIGS. 1 and 2 are merely examples. The conventional ultrasound diagnosis apparatus 100 may perform a frequency modulating processing at a stage preceding the A/D converters 22*b*, so as to change the sampling frequency used by the A/D converters 22*b*. Alternatively, the conventional ultrasound diagnosis apparatus 100 may reduce the number of times the calculation is performed by providing a wave detector at a stage preceding the adder 22*c* and providing a circuit in which the adder 22*c*, the signal processing unit 24, and the image generating unit 25 are combined together. In the conventional system, when a frequency modulating processing is performed before the A/D conversion, a circuit having a function substantially equivalent to that of the wave detector 230 is provided at a stage preceding the A/D converters 22*b*, so as to change the sampling frequency used by the A/D converters 22*b* in accordance with the spatial frequency subject to the actual imaging processing.

As explained above, generally speaking, the frequency $f_0$ of the reference signals used in the quadrature demodulation processing is conventionally set to be the center frequency of the ultrasound received signal. Furthermore, as explained above, according to the conventional technique, if the spatial frequency subject to an imaging processing has been changed due to a change in the setting, by changing the decimation rate of the decimation circuit 233, an amount of data reduction is sustained and the spatial resolution is adjusted.

Figure 4:
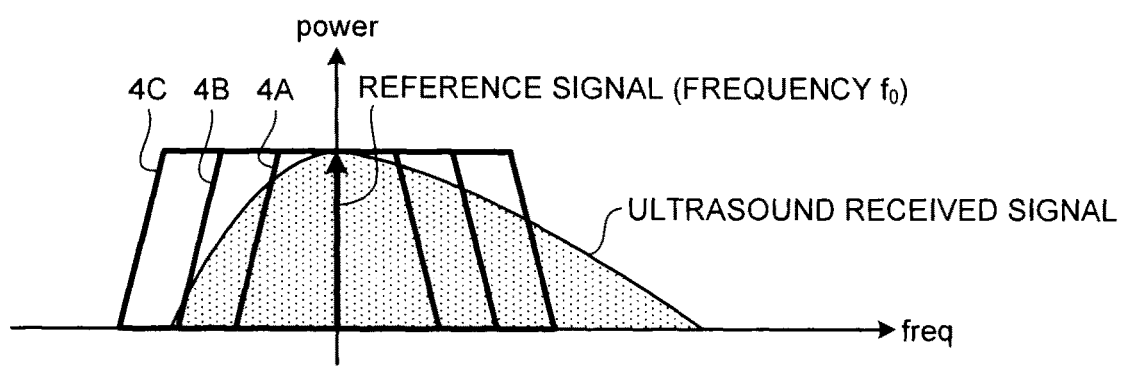
FIG. 4 and FIG. 5 are drawings for explaining a problem with a conventional technique.
Figure 5:
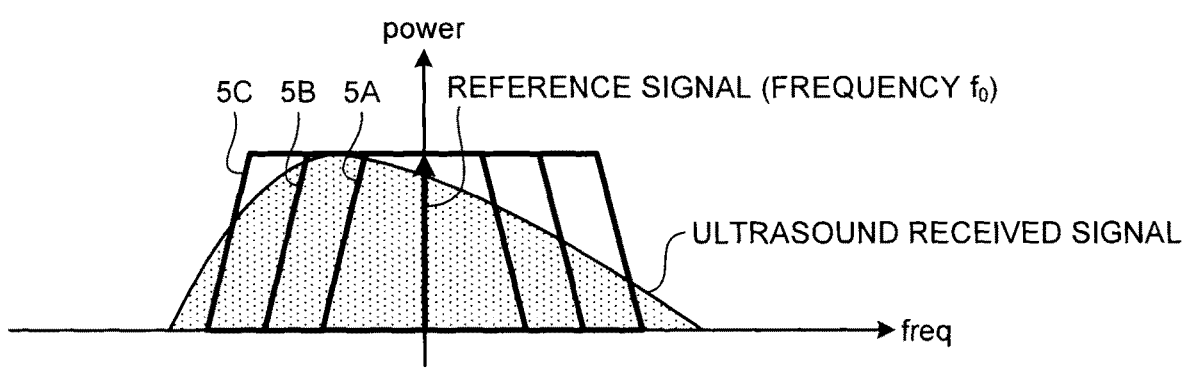

However, when the condition for setting the frequency of the reference signals used in the quadrature demodulation processing is fixed like in the conventional example, it is difficult, in some situations, to acquire an optimal signal band at all times, depending on the decimation rate. This aspect will be explained in detail, with reference to FIGS. 4 and 5. FIGS. 4 and 5 are drawings for explaining a problem with the conventional technique.

The ultrasound received signals in FIGS. 4 and 5 (see the "area with dotted hatching" in each of the drawings) are results of quadrature demodulation processing performed on ultrasound received signals having mutually the same frequency characteristic up to "a certain depth" determined by "a certain observation time", while using reference signals having mutually-different frequencies. Furthermore, FIGS. 4 and 5 illustrate passbands that are set by performing decimation processing at mutually-different decimation rates on the ultrasound received signals obtained after the quadrature demodulation processing.

In this situation, FIG. 4 illustrates "an example with a high decimation rate", i.e., the frequency $f_0$ of the reference signals used in the quadrature demodulation processing is set while prioritizing "the situation where deep parts are displayed with a low spatial resolution". In contrast, FIG. 5 illustrates "an example with a low decimation rate", i.e., the frequency $f_0$ of the reference signals used in the quadrature demodulation processing is set while prioritizing "the situation where shallow parts are displayed with a high spatial resolution or where the image is zoomed".

In FIG. 4, "4A, 4B, and 4C" indicate passbands that are set by further performing decimation processing at mutually-different decimation rates, on the ultrasound received signal obtained after the quadrature demodulation processing shown in FIG. 4. In FIG. 5, "5A, 5B, and 5C" indicate passbands that are set by further performing decimation processing at mutually-different decimation rates, on the ultrasound received signal obtained after the quadrature demodulation processing shown in FIG. 5. The passbands 4A and 5A each indicate a situation where, as a result of the sampling frequency being lowered due to a high decimation rate, the passband has become narrower. In contrast, the passbands 4C and 5C each indicate a situation where, as a result of the sampling frequency being raised due to a low decimation rate, the passband has become wider. The passband 4B indicates a passband set by a decimation rate between the decimation rate for the passband 4A and the decimation rate for the passband 4C. The passband 5B indicates a passband set by a decimation rate between the decimation rate for the passband 5A and the decimation rate for the passband 5C.

As illustrated in FIG. 4, the passband 4A is a band that is capable of effectively passing high sensitivity frequencies (i.e., frequencies having high intensities) in the ultrasound received signal and that blocks out-of-band regions (noise regions). In contrast, as illustrated in FIG. 4, the passband 4C is a band that passes out-of-band regions (noise regions) and that blocks frequency bands that are usable in an imaging processing. In this situation, the frequency $f_0$ of the reference signals shown in FIG. 4 is a frequency set by using the high decimation rate while prioritizing setting the passband 4A. As a result, if the decimation rate is lowered due to a change in the spatial frequency subject to the imaging processing, the passband will be the passband 4B or the passband 4C. The signal band passed by the passband 4C is not necessarily optimal and is a band that degrades sensitivity.

In contrast, as shown in FIG. 5, the passband 5C is a band that is able to effectively pass high sensitivity frequencies (i.e., the frequencies having high intensities) in the ultrasound received signal. However, the passband 5A passes low-sensitivity frequency bands (frequency bands having low intensities), even though there are other frequency bands with higher levels of sensitivity in the ultrasound received signal. Thus, the passband 5A is a band that degrades the sensitivity and the resolution. In this situation, the frequency $f_0$ of the reference signals shown in FIG. 5 is a frequency that is set by lowering the decimation rate while prioritizing setting the passband 5C. As a result, if the decimation rate is raised due to a change in the spatial frequency subject to the imaging processing, the passband will be the passband 5B or the passband 5A. The signal band passed by the passband 5A is not necessarily optimal and is a band that degrades sensitivity.

As explained above, according to the conventional technique, the frequency of the reference signals is fixed to the center frequency of the ultrasound received signal, regardless of the decimation rate. Consequently, according to the conventional technique, the frequency passband is not necessarily in an optimal setting, depending on the decimation rate. In other words, according to the conventional technique, the sensitivity and the spatial resolution of ultrasound image data are not optimal in some situations, depending on the decimation rate.

Figure 6:
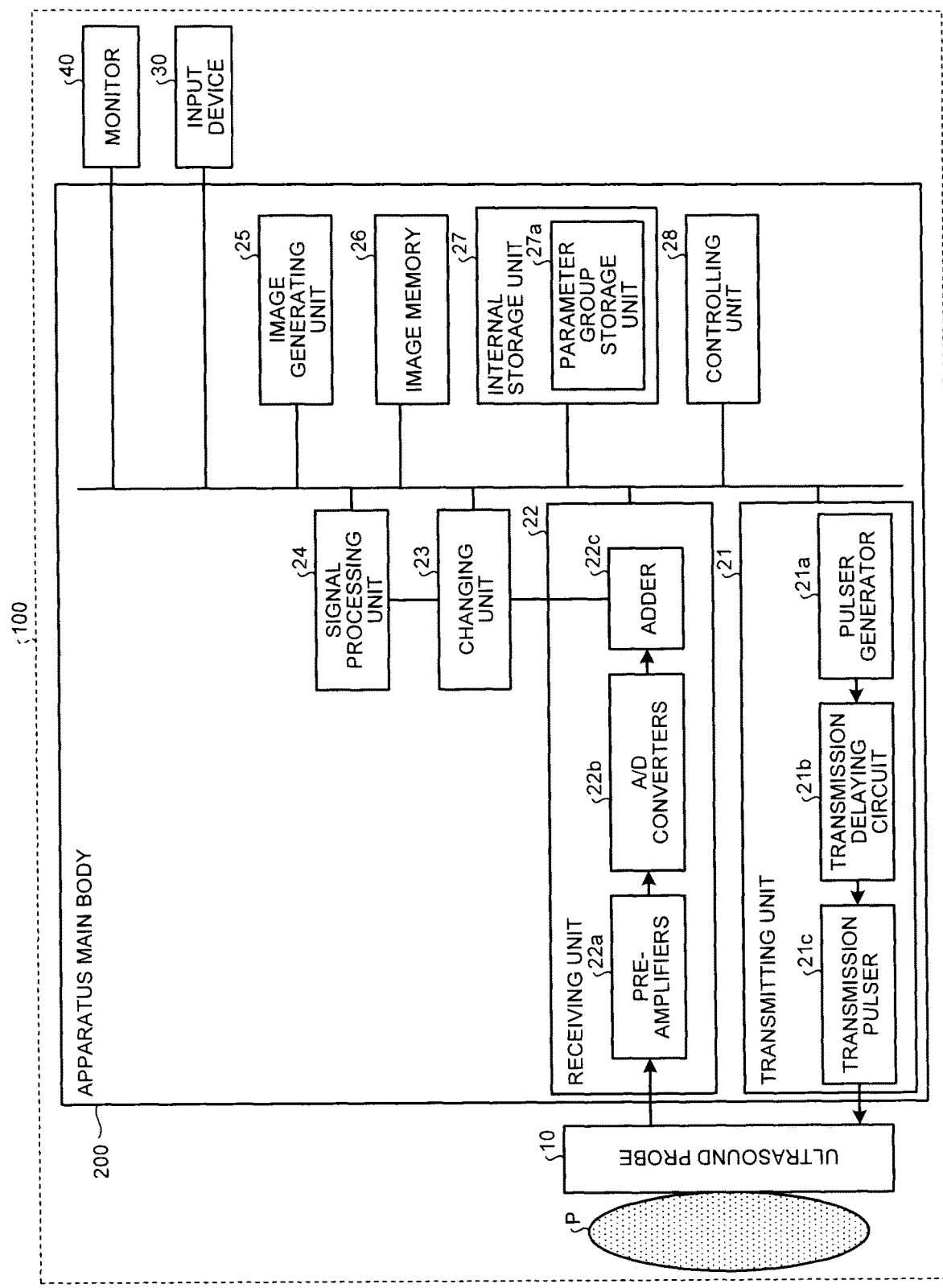
FIG. 6 is a drawing for explaining an exemplary configuration of an ultrasound diagnosis apparatus according to an embodiment.

To cope with this situation, according to an aspect of the exemplary embodiments discussed herein, the following processing is performed for the purpose of optimizing the sensitivity and the spatial resolution of ultrasound image data. FIG. 6 is a drawing for explaining an exemplary configuration of an ultrasound diagnosis apparatus according to an exemplary embodiment.

As shown in FIG. 6, an ultrasound diagnosis apparatus 1 according to the present embodiment includes, like the conventional ultrasound diagnosis apparatus 100 explained above, the ultrasound probe 10, the input device 30, and the monitor 40. Furthermore, instead of the apparatus main body 20 included in the conventional ultrasound diagnosis apparatus 100, the ultrasound diagnosis apparatus 1 according to the present embodiment includes an apparatus main body 200.

Like the apparatus main body 20 illustrated in FIG. 1, the apparatus main body 200 illustrated in FIG. 6 includes the receiving unit 22, the transmitting unit 21, the signal processing unit 24, the image generating unit 25, the image memory 26, and the controlling unit 28. The receiving unit 22, the transmitting unit 21, the signal processing unit 24, the image generating unit 25, the image memory 26, and the controlling unit 28 illustrated in FIG. 6 are the same as the receiving unit 22, the transmitting unit 21, the signal processing unit 24, the image generating unit 25, the image memory 26, and the controlling unit 28 explained with reference to FIG. 1.

Furthermore, like the apparatus main body 20 illustrated in FIG. 1, the apparatus main body 200 illustrated in FIG. 6 includes the internal storage unit 27. The internal storage unit 27 illustrated in FIG. 6 stores therein the various types of data stored in the internal storage unit 27 illustrated in FIG. 1. It should be noted, however, that the internal storage unit 27 illustrated in FIG. 6 includes a parameter group storage unit 27a, unlike the internal storage unit 27 illustrated in FIG. 1.

Furthermore, the apparatus main body 200 illustrated in FIG. 6 includes a changing unit 23, instead of the wave detector 230. The ultrasound diagnosis apparatus 1 according to the present embodiment is configured so that the changing unit 23 performs the processing described below while using a group of parameters stored in the parameter group storage unit 27a.

The changing unit 23 obtains a group of parameters related to frequency characteristics of ultrasound received signals used in an imaging processing (hereinafter, an "imaging received signal"), in accordance with a change in the spatial frequency of ultrasound image data subject to the imaging processing. The receiving unit 22 outputs the ultrasound received signal. The imaging received signal is an ultrasound received signal that is output by the receiving unit 22 as the ultrasound received signal to be used in the imaging processing, in accordance with a change in the spatial frequency of the ultrasound image data subject to the imaging processing. For example, the imaging received signal is an ultrasound received signal that is output by the adder 22c in accordance with a change in the spatial frequency. Furthermore, according to the present embodiment, the changing unit 23 obtains the group of parameters for the imaging received signal, by referring to the parameter group storage unit 27a. The parameter group storage unit 27a stores therein groups of parameters related to frequency characteristics of each of ultrasound received signals corresponding to ultrasound transmission/reception conditions. The changing unit 23 obtains, from the parameter group storage unit 27a, the group of parameters corresponding to the ultrasound transmission/reception condition of the imaging received signal, in accordance with the change in the spatial frequency of the ultrasound image data subject to the imaging processing. Furthermore, the changing unit 23 changes the center frequency and the frequency band used in the imaging processing performed on the imaging received signal, on the basis of the obtained group of parameters. In this manner, the changing unit 23 changes (performs a frequency demodulating processing on) the sampling frequency for the imaging received signal, which is digital data. In this situation, when having received a setting request that involves a change in the spatial frequency, the changing unit 23 changes the center frequency and the frequency band to be used in the imaging processing. Examples of setting requests that involve a change in the spatial frequency include a depth change request, a pan processing request, a zoom processing request, and an image output region change request each of which can be made by the operator via the input device 30.

In this situation, as the center frequency to be used in the imaging processing, the changing unit 23 according to the present embodiment determines the frequency of reference signals used in the quadrature demodulation processing performed on the imaging received signal, on the basis of the obtained group of parameters. Furthermore, as the frequency band to be used in the imaging processing, the changing unit 23 according to the present embodiment determines a passband set as a result of the quadrature demodulation processing and a decimation processing performed on the imaging received signal, on the basis of the obtained group of parameters.

Figures 7, 8:
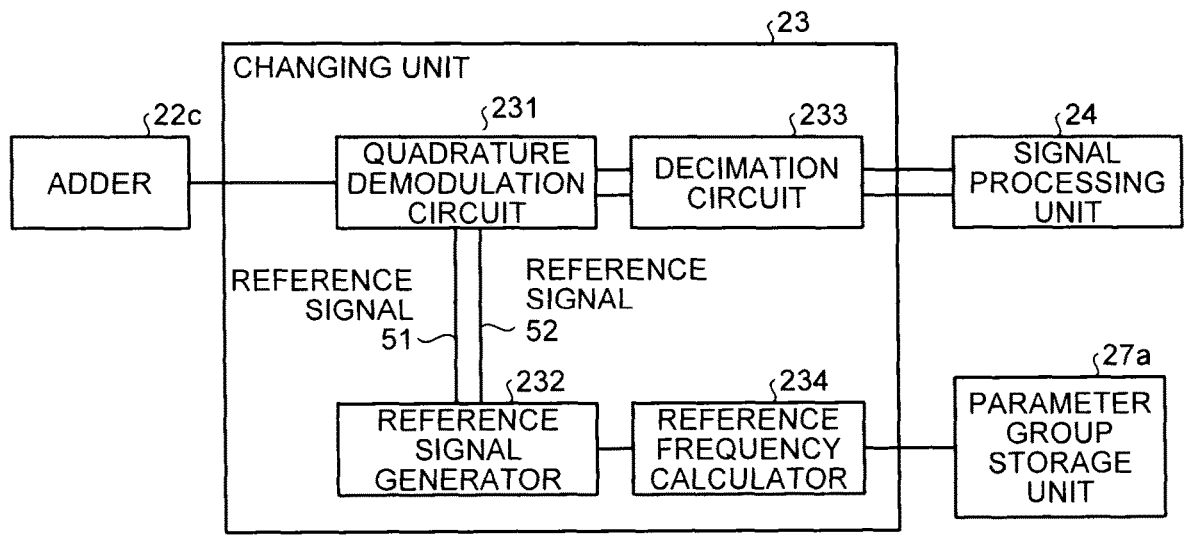
FIG. 7 is a diagram of an exemplary configuration of a changing unit according to the present embodiment.
FIG. 8 is a list of an example of a group of parameters stored in a parameter group storage unit.

In other words, the changing unit 23 performs the quadrature demodulation processing and the decimation processing in the same manner as the wave detector 230 does. FIG. 7 is a diagram of an exemplary configuration of the changing unit according to the present embodiment.

As illustrated in FIG. 7, the changing unit 23 includes the quadrature demodulation circuit 231, the reference signal generator 232, and the decimation circuit 233. As understood from the use of the same reference numerals, the quadrature demodulation circuit 231, the reference signal generator 232, and the decimation circuit 233 included in the changing unit 23 are the same circuits as the quadrature demodulation circuit 231, the reference signal generator 232, and the decimation circuit 233 included in the wave detector 230 illustrated in FIG. 2.

It should be noted, however, that the changing unit 23 according to the present embodiment includes a reference frequency calculator 234 as illustrated in FIG. 7, unlike the wave detector 230. The reference frequency calculator 234 determines the frequency of the reference signals on the basis of the group of parameters obtained from the parameter group storage unit 27a. Furthermore, the reference frequency calculator 234 transfers the determined frequency of the reference signals to the reference signal generator 232.

On the basis of the frequency of the reference signals received from the reference frequency calculator 234, the reference signal generator 232 generates a reference signal 51 and a reference signal 52 shown in FIG. 7. The quadrature demodulation circuit 231 performs a quadrature demodulation processing that uses the reference signals 51 and 52 on the ultrasound received signal (the imaging received signal) output from the adder 22c.

According to the conventional technique, the reference signal generator 232 generates the reference signal 501 and the reference signal 502, on the basis of the frequency that is set in advance. In contrast, according to the present embodiment, the reference signal generator 232 generates the reference signal 51 and the reference signal 52, on the basis of the frequency received from the reference frequency calculator 234.

Next, the group of parameters used by the reference frequency calculator 234 to determine the frequency of the reference signals and the method used by the reference frequency calculator 234 to determine the frequency of the reference signals while using the group of parameters will be explained more specifically. In the following sections, a "frequency of reference signals" will simply be referred to as a "reference frequency".

The groups of parameters stored in the parameter group storage unit 27a are made up of a plurality of pieces of information that are related to the frequency characteristics of the ultrasound received signal which is obtained, in advance, in correspondence with various ultrasound transmission/reception conditions. And, the groups of parameters are made up of a plurality of pieces of information used for determining the reference frequency. It is possible to obtain the groups of parameters on the basis of, for example, ultrasound received signals acquired by performing ultrasound transmissions/receptions on various phantoms while using various ultrasound transmission/reception conditions. Alternatively, it is also possible to obtain the groups of parameters, on the basis of ultrasound received signals acquired by performing ultrasound transmissions/receptions on the subject P who actually undergoes an ultrasound examination, while using various ultrasound transmission/reception conditions.

The groups of parameters obtained from such a processing are stored into the parameter group storage unit 27a. FIG. 8 is a list of an example of a group of parameters stored in the parameter group storage unit.

As shown in FIG. 8, an example of the parameters included in a group of parameters is a "peak frequency having the n-th highest intensity" of the ultrasound received signal. If "n=1" is satisfied, the peak frequency corresponds to the fundamental frequency, for example. If "n=2" is satisfied, the peak frequency corresponds to the second harmonic frequency, for example.

Furthermore, as shown in FIG. 8, another example of the parameters included in a group of parameters is a "center of mass frequency" of the ultrasound received signal. As shown in FIG. 8, other examples of the parameters included in a group of parameters are the "bandwidth" of the ultrasound received signal and a "fractional bandwidth" of the ultrasound received signal. The "bandwidth" of the ultrasound received signal may be "a bandwidth at −6 decibel (dB)" or "a bandwidth at −20 dB". The "fractional bandwidth" of the ultrasound received signal may be "a fractional bandwidth at −6 dB" or "a fractional bandwidth at −20 dB".

Furthermore, as shown in FIG. 8, other examples of the parameters included in a group of parameters are an "upper limit frequency" of the ultrasound received signal and a "lower limit frequency" of the ultrasound received signal. The "upper limit frequency" and the "lower limit frequency" serve as an upper limit value and a lower limit value of the frequency region of the ultrasound received signal which is desired to be imaged, within the frequency band of the ultrasound received signal.

The parameters included in a group of parameters do not necessarily have to be information about frequency characteristics per se of the ultrasound received signal. As shown in FIG. 8, for example, one of the parameters may be the "transmission frequency" or a "frequency equal to an integer multiple of the transmission frequency" from which it is possible to estimate the "peak frequency", the "upper limit frequency", and the "lower limit frequency". For example, "a frequency twice as high as the transmission frequency" corresponds to second harmonic used in a harmonic imaging processing. For example, if three types of items such as an "upper limit frequency", a "lower limit frequency", and a "peak frequency" are set as the items in a group of parameters, the parameter group storage unit 27*a* stores therein, for example, "an upper limit frequency, a lower limit frequency, and a peak frequency" calculated from an ultrasound received signal obtained under "ultrasound transmission/reception condition: C1"; "an upper limit frequency, a lower limit frequency, and a peak frequency" calculated from an ultrasound received signal obtained under "ultrasound transmission/reception condition: C2"; and "an upper limit frequency, a lower limit frequency, and a peak frequency" calculated from an ultrasound received signal obtained under "ultrasound transmission/reception condition: C3".

Figure 9:
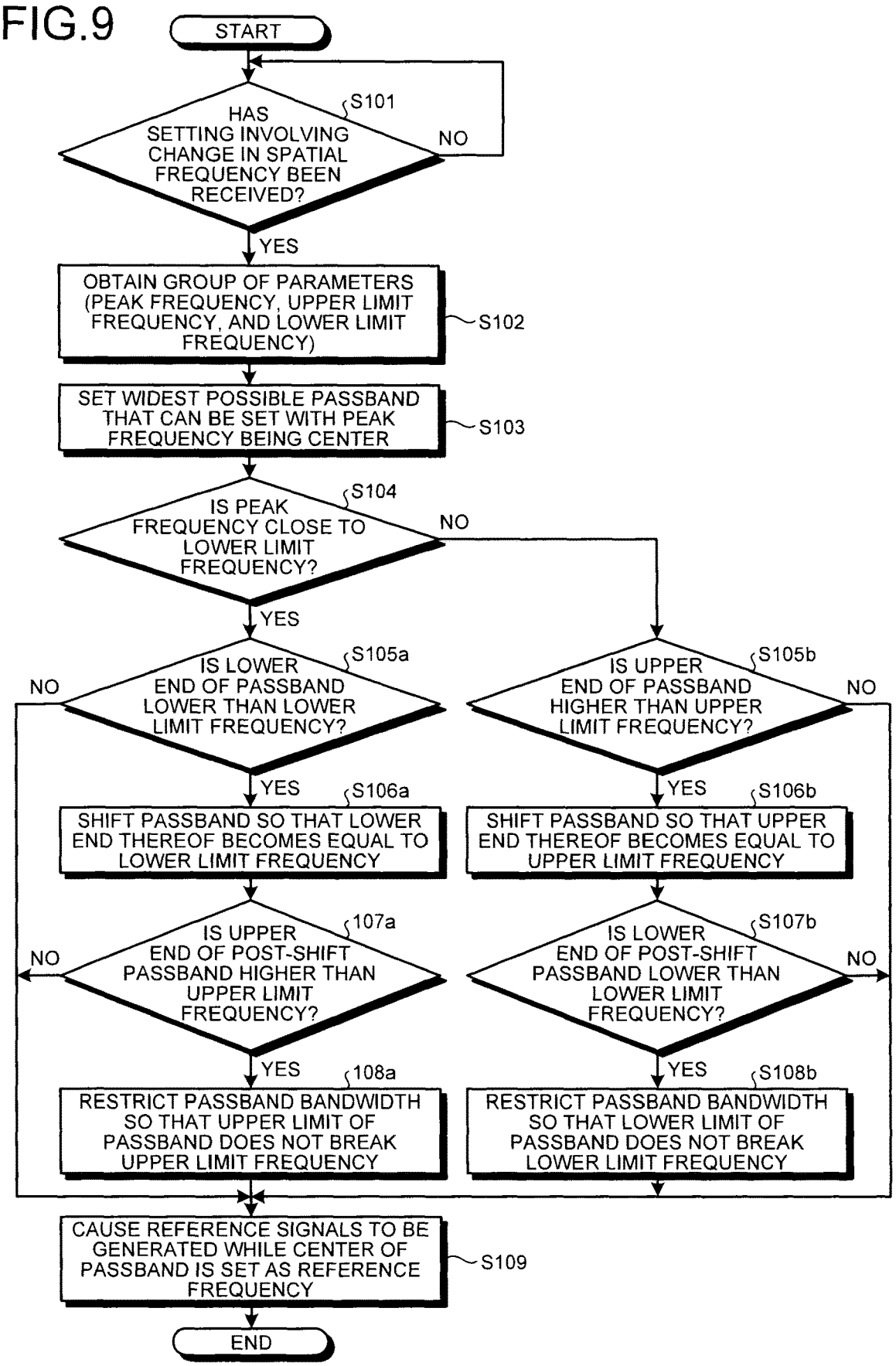
FIG. 9 is a flowchart of examples of processing performed by the changing unit according to the present embodiment.

The changing unit 23 determines the reference frequency by using one or more parameters from the group of parameters shown in FIG. 8. In the following sections, with reference to FIGS. 9, 10A, 10B, 10C, and 10D, an example will be explained in which the changing unit 23 determines the reference frequency while using a group of parameters made up of "a peak frequency (n=1)", "an upper limit frequency", and "a lower limit frequency" of the ultrasound received signal. FIG. 9 is a flowchart of examples of processing performed by the changing unit according to the present embodiment. FIGS. 10A to 10D are charts for explaining examples of transitions of a passband that are made according to the flowchart in FIG. 9.

As shown in FIG. 9, the controlling unit 28 included in the ultrasound diagnosis apparatus 1 according to the present embodiment judges whether a setting that involves a change in the spatial frequency of ultrasound image data subject to an imaging processing has been received from the operator via the input device 30 (step S101). If no such setting that involves a change in the spatial frequency has been received (step S101: No), the controlling unit 28 stands by until such a setting is received.

On the contrary, if a setting that involves a change in the spatial frequency has been received (step S101: Yes), the reference frequency calculator 234 obtains, under the control of the controlling unit 28, a group of parameters (a peak frequency, an upper limit frequency, and a lower limit frequency) that is kept in correspondence with the ultrasound transmission/reception condition used for receiving the imaging received signal serving as a processing target (step S102). In this situation, the "imaging received signal" is an ultrasound received signal acquired by using the ultrasound transmission/reception condition that was changed according to the setting involving the change in the spatial frequency.

Figure 10A:
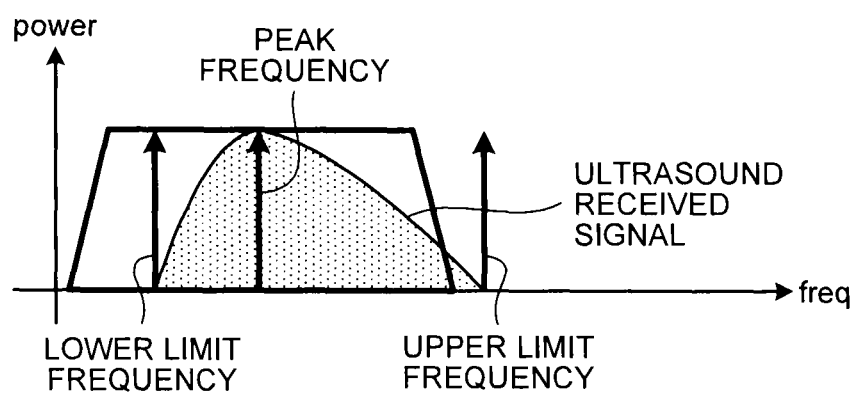
FIG. 10A, FIG. 10B, FIG. 10C and FIG. 10D are charts for explaining examples of transitions of a passband that are made according to the flowchart in FIG. 9.
Figure 10B:
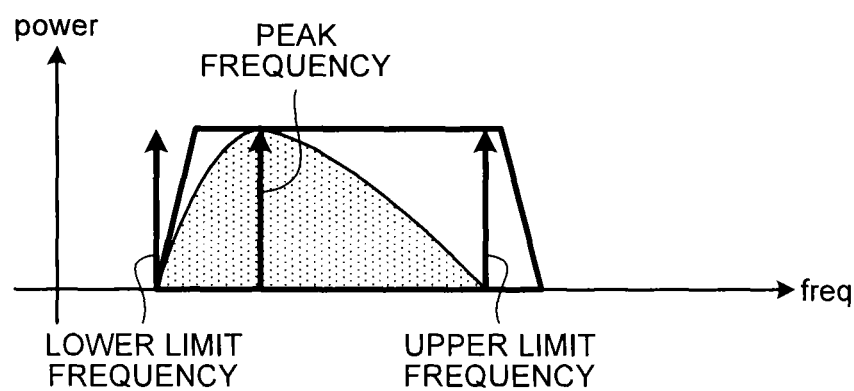

After that, the reference frequency calculator 234 sets the widest possible passband, the obtained peak frequency being the center (step S103). In this situation, the "widest possible passband that can be set" means the widest possible region that can be set within a range that satisfies the sampling theorem, on the basis of the sampling frequency and the decimation rate used by the A/D converters 22*b* included in the receiving unit 22. In FIG. 10A, the peak frequency, the upper limit frequency, and the lower limit frequency of the ultrasound received signal (the imaging received signal) is indicated with upward arrows. For example, "the peak frequency, the upper limit frequency, and the lower limit frequency" shown in FIG. 10A are "the peak frequency, the upper limit frequency, and the lower limit frequency" that are kept in correspondence with the "ultrasound transmission/reception condition: C3" that is the same as or similar to the ultrasound transmission/reception condition for the imaging received signal. In FIG. 10A, the "widest possible passband that can be set" mentioned above is indicated with a trapezoidal frame.

After that, the reference frequency calculator 234 judges whether the peak frequency is a frequency close to the lower limit frequency (step S104). If the peak frequency is a frequency close to the lower limit frequency (step S104: Yes), the reference frequency calculator 234 judges whether the lower end of the passband set at step S103 is lower than the lower limit frequency (step S105*a*).

In this situation, if the lower end of the passband set at step S103 is a frequency equal to or higher than the lower limit frequency (step S105*a*: No), the reference frequency calculator 234 determines that the passband set at step S103 is a band positioned between the upper limit frequency and the lower limit frequency of the imaging received signal. After that, the reference frequency calculator 234 causes the reference signal generator 232 to generate reference signals, while setting the center of the passband set at step S103 as the reference frequency (step S109) and thus ends the processing.

On the contrary, if the lower end of the passband set at step S103 is lower than the lower limit frequency (step S105*a*: Yes), the reference frequency calculator 234 shifts the passband set at step S103 so that the lower end thereof becomes equal to the lower limit frequency (step S106*a*; see FIG. 10B).

After that, the reference frequency calculator 234 judges whether the upper end of the passband shifted at step S106*a* is higher than the upper limit frequency (step S107*a*). In this situation, if the upper end of the passband shifted at step S106*a* is a frequency equal to or lower than the upper limit frequency (step S107*a*: No), the reference frequency calculator 234 determines that the passband set at step S106*a* is a band positioned between the upper limit frequency and the lower limit frequency of the imaging received signal. After that, the reference frequency calculator 234 causes the reference signal generator 232 to generate reference signals, while setting the center of the passband set at step S106*a* as the reference frequency (step S109) and thus ends the processing.

Figure 10C:
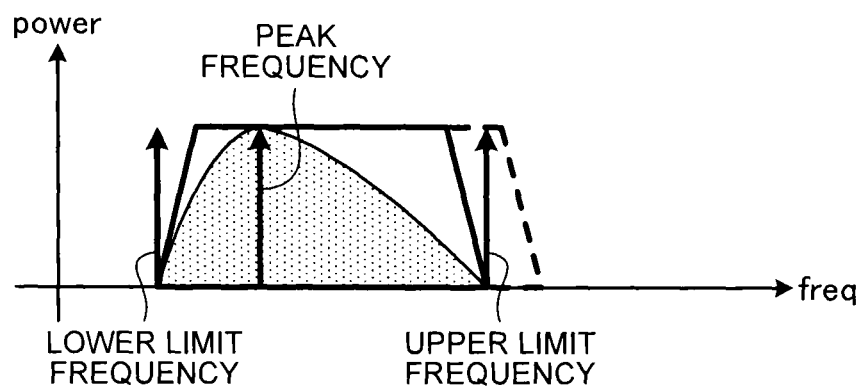
Figure 10D:
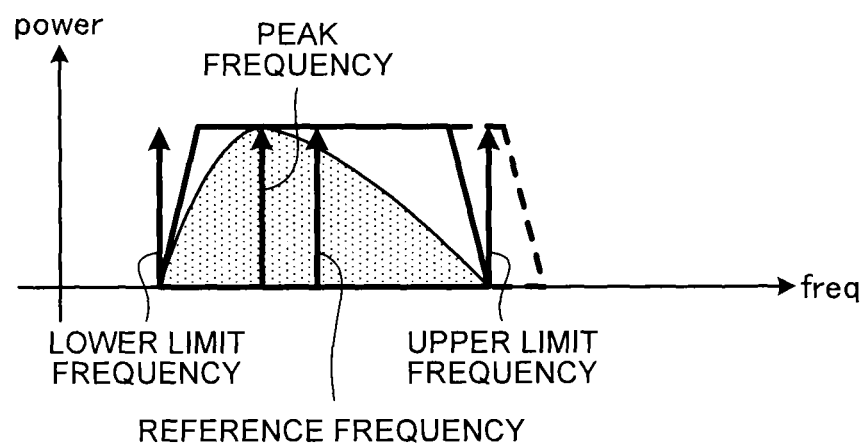

On the contrary, if the upper end of the passband shifted at step S106*a* is higher than the upper limit frequency (step S107*a*: Yes), the reference frequency calculator 234 restricts the passband bandwidth shifted at step S106*a* so that the upper limit of the passband shifted at step S106*a* does not break the upper limit frequency (step S108*a*; see FIG. 10C). In FIG. 10C, the passband before the band restriction is indicated with a broken line, whereas the passband after the band restriction is indicated with a solid line. In this situation, the upper limit frequency and the lower limit frequency define a signal region desired to be imaged. The outside of the upper limit frequency and the lower limit frequency corresponds to noise regions, which are not desired to be imaged. For this reason, from the viewpoint of optimizing the signal-to-noise ratio (S/N), it is desirable to block the noise regions by narrowing the passband, as shown in FIG. 10C. Thus, with the processing at step S108a (and the processing at step S108b described below), the passband is restricted so as to be in the region within the "upper limit frequency" and the "lower limit frequency". In this situation, since the passband set at step S103 is set to the "widest possible passband that can be set", it is not possible to widen the passband; however, it is possible to narrow the passband by setting filter coefficients.

After that, the reference frequency calculator 234 causes the reference signal generator 232 to generate reference signals, while setting the center of the passband restricted at step S108a as the reference frequency (see FIG. 10D) (step S109) and thus ends the processing.

On the contrary, if the peak frequency is a frequency close to the upper limit frequency (step S104: No), the reference frequency calculator 234 judges whether the upper end of the passband set at step S103 is higher than the upper limit frequency (step S105b).

In this situation, if the upper end of the passband set at step S103 is a frequency equal to or lower than the upper limit frequency (step S105b: No), the reference frequency calculator 234 determines that the passband set at step S103 is a band positioned between the upper limit frequency and the lower limit frequency of the imaging received signal. After that, the reference frequency calculator 234 causes the reference signal generator 232 to generate reference signals, while setting the center of the passband set at step S103 as the reference frequency (step S109) and thus ends the processing.

On the contrary, if the upper end of the passband set at step S103 is higher than the upper limit frequency (step S105b: Yes), the reference frequency calculator 234 shifts the passband set at step S103 so that the upper end thereof becomes equal to the upper limit frequency (step S106b).

After that, the reference frequency calculator 234 judges whether the lower end of the passband shifted at step S106b is lower than the lower limit frequency (step S107b). In this situation, if the lower end of the passband shifted at step S106b is a frequency equal to or higher than the lower limit frequency (step S107b: No), the reference frequency calculator 234 determines that the passband set at step S106b is a band positioned between the upper limit frequency and the lower limit frequency of the imaging received signal. Furthermore, the reference frequency calculator 234 causes the reference signal generator 232 to generate reference signals, while setting the center of the passband set at step S106b as the reference frequency (step S109) and thus ends the processing.

On the contrary, if the lower end of the passband shifted at step S106b is lower than the lower limit frequency (step S107b: Yes), the reference frequency calculator 234 restricts the passband bandwidth shifted at step S106b so that the lower limit of the passband shifted at step S106b does not break the lower limit frequency.

Furthermore, the reference frequency calculator 234 causes the reference signal generator 232 to generate reference signals, while setting the center of the passband restricted at step S108b as the reference frequency (step S109) and thus ends the processing.

As explained above, the changing unit 23 determines the frequency band that includes the peak frequency of the imaging received signal and that does not break the upper limit frequency and the lower limit frequency of the imaging received signal, as the frequency band to be used in the imaging processing. After that, the changing unit 23 determines the center frequency of the determined frequency band as the center frequency to be used in the imaging processing. In other words, according to the present embodiment, as a result of the processing shown in FIG. 9, it is possible to set a passband on the inside of the range from the lower limit frequency to the upper limit frequency at all times, while arranging the peak frequency to be within the passband. As a result, according to the present embodiment, it is possible to generate the ultrasound image data by outputting the reflected-wave data to the signal processing unit 24 provided at the subsequent stage, while minimizing the degradation of the S/N and maintaining an optimal spatial resolution at all times. As a result, according to the present embodiment, it is possible to optimize the sensitivity and the spatial resolution of the ultrasound image data.

Next, specific examples of passbands determined as a result of the processing shown in FIG. 9 will be further explained, with reference to FIGS. 11A, 11B, 11C, and 11D. FIGS. 11A, 11B, 11C, and 11D are charts of the specific examples of passbands determined as a result of processing performed by the changing unit according to the present embodiment.

Figure 11A:
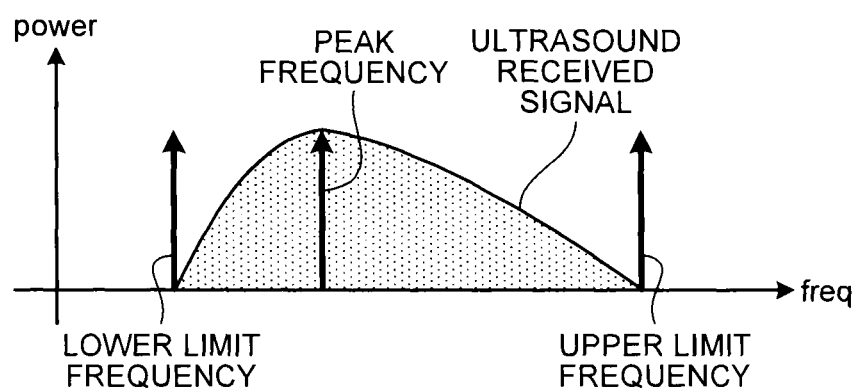
FIG. 11A, FIG. 11B, FIG. 11C and FIG. 11D are charts of specific examples of passbands determined as a result of processing performed by the changing unit according to the present embodiment.

For example, let us discuss an example in which the changing unit 23 has received an ultrasound received signal having a frequency characteristic shown in FIG. 11A. The frequency band of the ultrasound received signal shown in FIG. 11A is equal to the frequency band of the ultrasound received signal shown in FIGS. 4 and 5.

On the basis of the ultrasound transmission/reception condition, the reference frequency calculator 234 obtains a peak frequency, a lower limit frequency, and an upper limit frequency. After that, as shown in FIG. 11A, the reference frequency calculator 234 sets the peak frequency, the lower limit frequency, and the upper limit frequency that were obtained, with an ultrasound received signal. In this situation, FIGS. 11B, 11C, and 11D illustrate specific examples of passbands determined by the reference frequency calculator 234 when mutually-different decimation rates are set for the passbands (the passable bands).

Figure 11B:
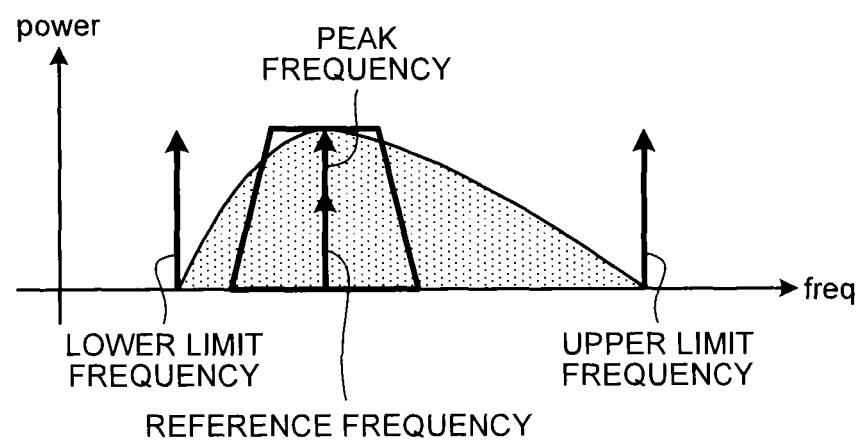
Figure 11C:
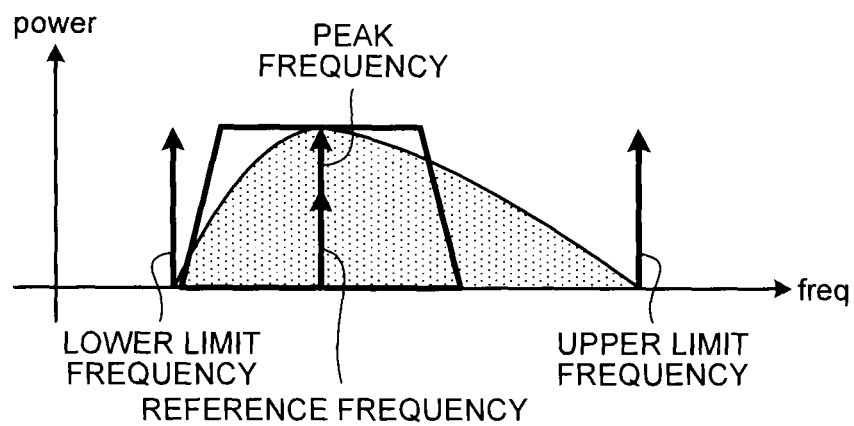
Figure 11D:
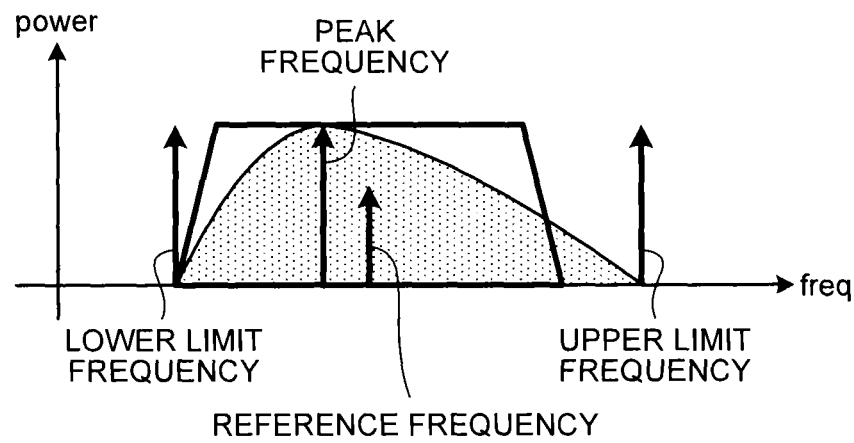

With reference to FIG. 11B, a method for determining a reference frequency when the decimation rate is set to be high, whereas the passband is set to be narrow will be explained. First, the reference frequency calculator 234 checks to see if the passband set, the "peak frequency" being the center, includes the "lower limit frequency" or the "upper limit frequency". In the example shown in FIG. 11B, because the passband does not include the "lower limit frequency" and the "upper limit frequency" even if the "peak frequency" is set at the center of the passband, the reference frequency calculator 234 determines the "peak frequency" as the reference frequency. In the example shown in FIG. 11C also, because the passband does not include the "lower limit frequency" and the "upper limit frequency" even if the "peak frequency" is set at the center of the passband, the reference frequency calculator 234 determines the "peak frequency" as the reference frequency.

In contrast, in the example shown in FIG. 11D, because the passband is set also below the "lower limit frequency" when the passband is set, "peak frequency" being the center, the reference frequency calculator 234 performs a shifting processing so that the lower limit of the passband becomes equal to the "lower limit frequency". In other words, while using the "lower limit frequency" as a criterion, the reference frequency calculator 234 determines a frequency band that is higher than the criterion frequency as the passband.

In this situation, the passband determined on the basis of the reference frequency shown in FIG. 11B is similar to the passband (the passband 4A shown in FIG. 4) obtained when the frequency of the reference signals is set while prioritizing a high decimation rate and a narrow passband. On the contrary, the passband determined on the basis of the reference frequency shown in FIG. 11D is similar to the passband (the passband 5C shown in FIG. 5) obtained when the frequency of the reference signals is set while prioritizing a low decimation rate and a wide passband.

As explained with reference to FIG. 11A to 11D, according to the present embodiment, it is possible to set the optimal reference frequencies, without being dependent on the thinning-out rates (the decimation rates).

According to the conventional technique, only the bandwidth of the ultrasound received signal is changed in accordance with a change in the spatial frequency subject to an imaging processing, and the band itself remains unchanged. For this reason, according to the conventional technique, the sensitivity and the spatial resolution of the ultrasound image data are not necessarily always optimal, depending on the change in the spatial frequency subject to an imaging processing.

In contrast, according to the present embodiment, as explained above, the reference frequency is changed in accordance with the change in the spatial frequency subject to an imaging processing, so as to change the passband into a "passband that is able to effectively pass high sensitivity frequencies and to block noise regions". As a result, according to the present embodiment, regardless of the changes in the spatial frequency subject to the imaging processing, it is possible to cause an optimal frequency band of the ultrasound received signal to be subject to an imaging processing at all times and to optimize the sensitivity and the spatial resolution of the ultrasound image data.

It is possible to implement the method for determining the reference frequency described above, by using one or a plurality of, the plurality of exemplary parameters listed in FIG. 8. Furthermore, it is possible to configure the present embodiment so that the processing performed by the changing unit 23 is performed at a stage preceding the adder 22c. For example, the imaging received signal may be an ultrasound received signal output by the pre-amplifiers 22a in accordance with a change in the spatial frequency. Alternatively, the imaging received signal may be, for example, an ultrasound received signal output by the A/D converters 22b in accordance with a change in the spatial frequency. Furthermore, in the exemplary embodiments above, the example is explained in which the reference frequency used in the quadrature demodulation processing is changed in accordance with the change in the spatial frequency. However, the exemplary embodiments are also applicable to a situation where the center frequency used for a frequency conversion employed in other processing that is capable of analyzing acoustic signals is changed in accordance with a change in the spatial frequency. Examples of such other processing described above include a process in which a frequency transformation, a Low Pass Filter (LPF), an envelope detecting processing, and the like are combined.

In recent years, downsizing of ultrasound diagnosis apparatuses is progressing. Examples of ultrasound diagnosis apparatuses that have been put in practical use include: an ultrasound diagnosis apparatus in which a part of the processing units that constitute the apparatus main body 20 is installed inside the ultrasound probe 10; and an ultrasound diagnosis apparatus in which the apparatus main body 20 is installed inside the ultrasound probe 10. When such an ultrasound diagnosis apparatus is used, for example, it is possible to realize the changing processing described above, by configuring the ultrasound probe 10 so as to have installed therein at least the transmitting unit 21, the receiving unit 22, and the changing unit 23 shown in FIG. 6.

Figure 12:
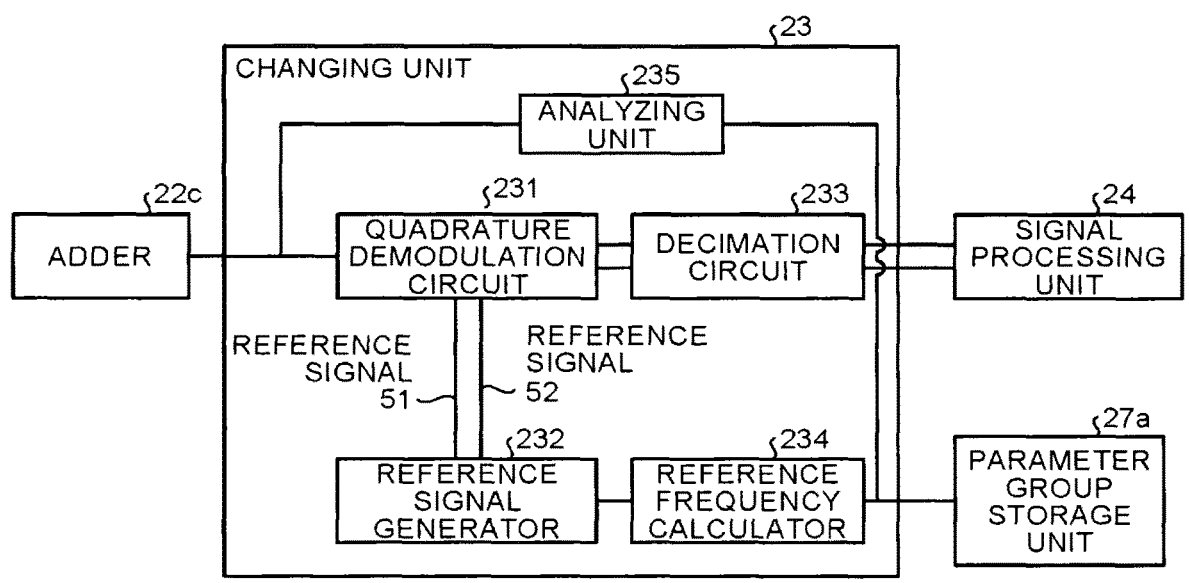
FIG. 12 is a diagram of an exemplary configuration of a changing unit according to a modification example.
Figure 13:
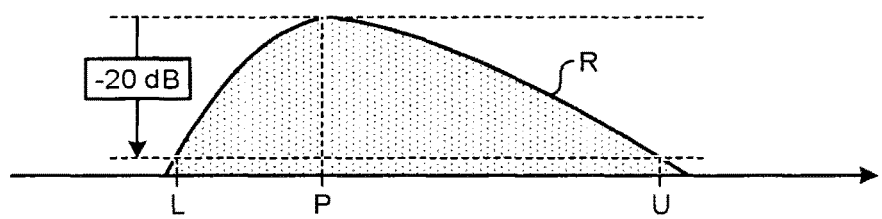
FIG. 13 is a chart for explaining the analyzing unit shown in FIG. 12.

In the exemplary embodiments described above, the example is explained in which the changing unit 23 obtains the group of parameters for the imaging received signal by referring to the parameter group storage unit 27a. In other words, in the exemplary embodiments above, the example is explained in which the group of parameters kept in correspondence with either the ultrasound transmission/reception condition of the imaging received signal or the ultrasound reception condition similar to the ultrasound transmission/reception condition of the imaging received signal is used as the group of parameters for the imaging received signal; however, in some situations, the frequency characteristics of the imaging received signal actually obtained may not necessarily coincide with the frequency characteristics of the ultrasound received signal obtained in advance under the ultrasound transmission/reception condition of the imaging received signal. To cope with these situations, the changing unit 23 may implement a modification example as described below. The changing unit 23 according to the modification example obtains a group of parameters for an imaging received signal serving as a target of an imaging processing, by performing a frequency analysis on the imaging received signal. This modification example will be explained, with reference to FIGS. 12 and 13. FIG. 12 is a diagram of an exemplary configuration of the changing unit according to the modification example. FIG. 13 is a chart for explaining the analyzing unit shown in FIG. 12.

As illustrated in FIG. 12, the changing unit 23 according to the modification example further includes an analyzing unit 235, being different from the configuration shown in FIG. 7. The analyzing unit 235 obtains a group of parameters for an imaging received signal serving as a target of an imaging processing by performing a frequency analysis on the imaging received signal. For example, the analyzing unit 235 obtains parameters corresponding to items specified by the operator, by performing the frequency analysis. Let us assume that an "upper limit frequency", a "lower limit frequency", and "a peak frequency" are specified. In that situation, as shown in FIG. 13, the analyzing unit 235 calculates a peak frequency P of an imaging received signal R, by performing the frequency analysis. After that, as shown in FIG. 13, the analyzing unit 235 calculates two frequencies having an intensity of "−20 dB", which is the intensity of the peak frequency P, as a lower limit frequency L and a upper limit frequency U. The dB value used for calculating the lower limit frequency L and the upper limit frequency U may arbitrarily be changed. Furthermore, the dB value used for calculating the lower limit frequency L and the dB value used for calculating the upper limit frequency U may be different from each other.

After that, the analyzing unit 235 notifies the reference frequency calculator 234 of the "upper limit frequency U", the "lower limit frequency L", and the "peak frequency P" calculated from the frequency analysis. Consequently, the reference frequency calculator 234 determines a passband, which is the frequency band to be used in the imaging processing, and a reference frequency, which is the center frequency to be used in the imaging processing. After that, the reference frequency calculator 234 notifies the reference signal generator 232 of the determined reference frequency.

The processing performed in the present modification example are the same as those in the flowchart in FIG. 9, except that the parameter group obtaining processing at step S102 is performed by the analyzing unit 235. Thus, the explanation thereof will be omitted.

As explained above, according to the present modification example, the group of parameters for the ultrasound received signal itself to be used in the imaging processing is calculated by performing the frequency analysis, so as to determine the passband and the reference frequency. As a result, according to the present modification example, it is possible to adaptively determine the passband and the reference frequency that are optimal in accordance with the characteristics of the image taking site of the subject P undergoing the image taking processing. Consequently, according to the present modification example, it is possible to optimize the sensitivity and the spatial resolution of the ultrasound image data with certainty. Furthermore, according to the present modification example, because there is no need to obtain, in advance, the groups of parameters corresponding to the various ultrasound transmission/reception conditions, it is possible to automate substantially all of the passband setting processing.

In this situation, the analyzing unit 235 may store the calculated group of parameters into the parameter group storage unit 27a. For example, the analyzing unit 235 may store the "upper limit frequency U", the "lower limit frequency L", and the "peak frequency P" into the parameter group storage unit 27a, while keeping these items in correspondence with the ultrasound transmission/reception condition of the imaging received signal R. As a result of processing performed in this manner, the parameter group storage unit 27a will be able to accumulate groups of parameters corresponding to various ultrasound transmission/reception conditions.

When the groups of parameters obtained from the frequency analysis are accumulated in this manner, the present modification example may be configured so as to use together the parameter group obtaining processing employing the analyzing unit 235 and the parameter group obtaining processing employing the parameter group storage unit 27a. In other words, the operator is able to select whether the analyzing unit 235 should be employed or the parameter group storage unit 27a should be employed. For example, when the operator wishes to prioritize real-time characteristics, the operator may select the processing employing the parameter group storage unit 27a. In contrast, when the operator wishes to prioritize the sensitivity and the spatial resolution of the ultrasound image data, the operator may select the processing employing the analyzing unit 235.

The contents of the exemplary embodiments described above are applicable to the present modification example, except that the group of parameters is obtained by performing the frequency analysis.

The constituent elements of the apparatuses that are shown in the drawings are based on functional concepts. Thus, it is not necessary to physically configure the elements as indicated in the drawings. In other words, the specific mode of distribution and integration of the apparatuses is not limited to the ones shown in the drawings. It is acceptable to functionally or physically distribute or integrate all or a part of the apparatuses in any arbitrary units, depending on various loads and the status of use. For example, the reference frequency calculator 234 may be incorporated in the controlling unit 28. Furthermore, all or an arbitrary part of the processing functions performed by the apparatuses may be realized by a Central Processing Unit (CPU) and a computer program that is analyzed and executed by the CPU or may be realized as hardware using wired logic.

As explained above, according to an aspect of the exemplary embodiments and the modification examples, it is possible to optimize the sensitivity and the spatial resolution of the ultrasound image data.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
   processing circuitry configured to:
   perform a beam-forming processing to output an ultrasound received signal to be used to generate ultrasound image data;
   obtain in accordance with a change in a spatial frequency of the ultrasound image data subject to an imaging processing, an upper limit frequency of the ultrasound received signal, a lower limit frequency of the ultrasound received signal, and a peak frequency of the ultrasound received signal, wherein the peak frequency has n-th highest intensity for n-th harmonic frequency, as a group of parameters, the group of parameters being related to a frequency characteristic of an imaging received signal that is output as the ultrasound received signal;
   change a frequency of a reference signal to be used in a quadrature demodulation processing performed on the imaging received signal and a bandwidth of a passband, on a basis of the upper limit frequency, the lower limit frequency, and the peak frequency, and
   perform, on a basis of the changed frequency and the changed bandwidth, the quadrature demodulation processing and a decimation processing, wherein the processing circuitry is further configured to:
   judge, when a center of the passband matches the peak frequency, whether the upper end of the passband is higher than the upper limit frequency, or whether the lower end of the passband is lower than the lower limit frequency;
   in a case the upper end of the passband is higher than the upper limit frequency or the lower end of the passband is lower than the lower limit frequency, change the bandwidth of the passband so as not to exceed the upper limit frequency or the lower limit frequency;
   determine a center frequency of the passband having the bandwidth changed, as the changed frequency of the reference signal, and;
   perform, on a basis of the changed frequency and the changed bandwidth, the quadrature demodulation processing.

2. The ultrasound diagnosis apparatus according to claim 1, further comprising: parameter group storage configured to store therein groups of parameters related to frequency characteristics of each of ultrasound received signals corresponding to ultrasound transmission/reception conditions, wherein the processing circuitry is configured to obtain the group of parameters corresponding to an ultrasound transmission/reception condition of the imaging received signal from the parameter group storage.

3. The ultrasound diagnosis apparatus according to claim 1, wherein the processing circuitry is configured to obtain the group of parameters of the imaging received signal by performing a frequency analysis on the imaging received signal.

4. The ultrasound diagnosis apparatus according to claim 1, wherein, in the case of receiving a setting request that involves a change in the spatial frequency, the processing circuitry is configured to change the frequency of the reference signal and the bandwidth of the passband.

* * * * *